United States Patent [19]
Zhao

[11] Patent Number: 5,313,951

[45] Date of Patent: May 24, 1994

[54] DEVICE AND A METHOD TO MEASURE THE INFRARED RADIATION OF THE HUMAN BODY

[76] Inventor: Shi Zhao, 706 Bldg. 12, Yue Tan Bei Jie, Beijing, China, 100045

[21] Appl. No.: 731,733

[22] Filed: Jul. 16, 1991

[30] Foreign Application Priority Data

Jul. 19, 1990 [CN] China .............................. 90216396.5
Nov. 29, 1990 [CN] China .............................. 90109472.2

[51] Int. Cl.⁵ .............................................. A61B 6/00
[52] U.S. Cl. ...................................... 128/664; 128/736
[58] Field of Search ........ 128/664, 736, 633, 665–667; 356/39–41

[56] References Cited

U.S. PATENT DOCUMENTS

| | | | |
|---|---|---|---|
| 2,804,069 | 8/1957 | Schwamm et al. | 128/664 |
| 5,024,533 | 6/1991 | Egawa et al. | 374/126 |
| 5,062,428 | 11/1991 | Chance | 128/664 |

Primary Examiner—Angela D. Sykes
Attorney, Agent, or Firm—Merchant, Gould, Smith, Edell, Welter & Schmidt

[57] ABSTRACT

The invention relates to a device and a method to measure the IR radiation flux in connection with the temperature difference on the human body surface. The device of the invention comprises an IR sensor, a display unit connected to the output terminal of the said IR sensor, and a test mount. The mount is placed tightly against the covering on the body. The device measures from outside the covering the IR radiation flux on the corresponding part of the human body, and the measurement results are shown on the display unit.

1 Claim, 3 Drawing Sheets

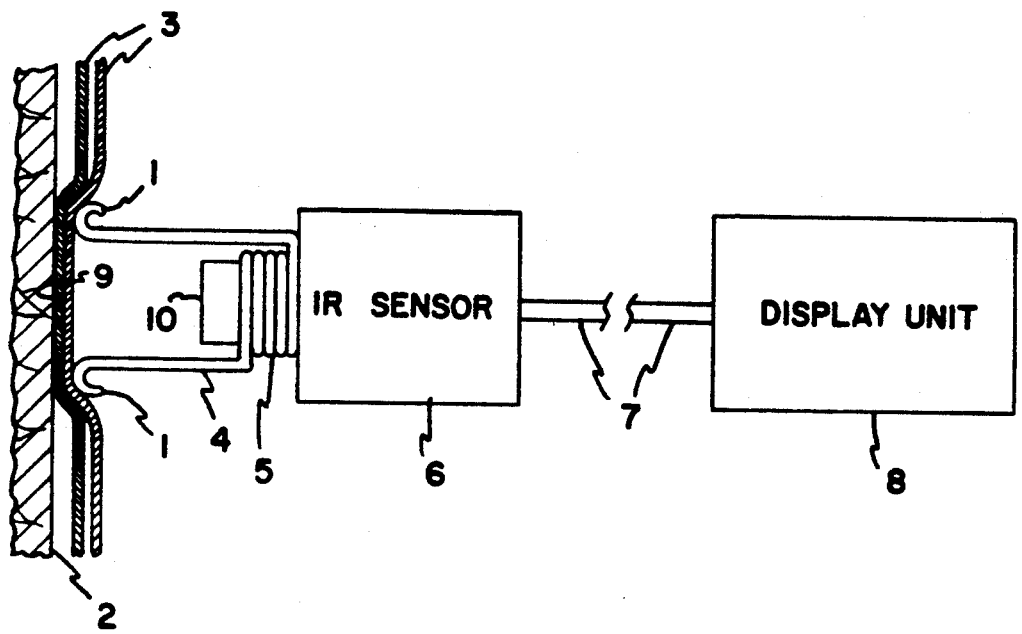
FIG. 2
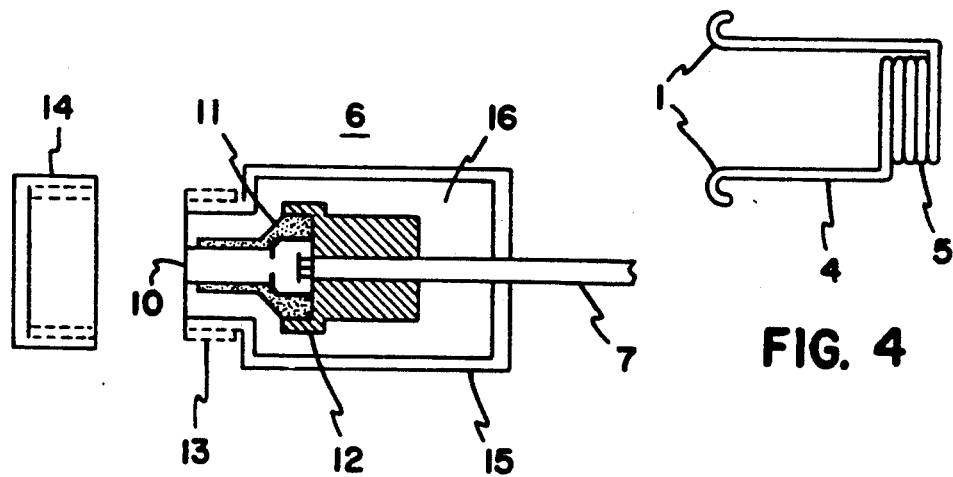
FIG. 3
FIG. 4

DEVICE AND A METHOD TO MEASURE THE INFRARED RADIATION OF THE HUMAN BODY

BACKGROUND OF THE INVENTION

The present invention relates to a device and a method to measure the infrared radiation flux in connection with the temperature difference on human body surface. More particularly, the present invention relates to a device and a method used to measure, from outside the covering on the human body, the IR radiation flux in connection with the skin temperature difference between the spot on the human body surface corresponding to a person's internal organ and its adjacent spots on the body surface.

Humans are animals with a constant body temperature. Human body temperature is maintained constant through a dynamic balance comprising processes of controlling heat generation and dissipation under the action of behaviour and self adjustment. From the physiological view, when a person is quiet, about 50% of his body heat is generated by his internal organs. At ambient temperatures of 16° to 25° C., more than 50% of the total dissipated body heat is dissipated through body skin radiation. From the pathological point of view, when a person is sick or the physiological state of his organs is changing, the metabolism of his internal organs and tissues and the amount of heat generated by them will also change, thus disrupting the thermal balance of part or the whole of the body. Clinically, this is reflected in the rise or fall of the temperature of the organ. Since the amount of heat generated by the various internal organs and the metabolization rate of the human body are different, the heat contribution or the micro heat increment of the various heat-generating organs is different in the corresponding shallow skin of the body. If such temperature variation in the various parts on the body surface is measured, important physiological data will therefore be provided for assessing the level of the metabolic function of a person's internal organs and his tissue energy.

A common method to measure the temperature of a human body is to use a rod-shaped mercury thermometer. Recent years have seen thermometers made of semiconductor materials or metal. Although these thermometers incorporate significant improvements in both operation method and accuracy, they are still not accurate enough to measure the heat contribution or the minute temperature difference (normally 0.01° to 0.05° C.) formed in the corresponding spots in the skin due to energy metabolism of the various internal organs and tissues.

People tried to resolve the minute temperature difference between the various parts in the body skin by using an IR thermal imager with a temperature resolution of 0.01° C. Unfortunately IR thermal imagers with such a high resolution are still unable to find the truth of the energy metabolism of a person's internal organs and tissues. This is because when an IR thermal imager is used to measure the temperature characteristics in the body skin (at room temperatures of 16° to 25° C.), the tested person has to bare part of his body for measurement and allow that part of his body to stay put for quite a long time. During the stay-put period, the body skin temperature of the tested person varies correspondingly with the varying ambient temperature as he is under the influence of the ambient temperature, humidity and air flow and also under the action of self adjustment as shown by the group of curves on the left side of FIG. 1A. This upsets to varying extents the micro heat increment (0.01° to 0.05° C.) that reflects the level of energy metabolism of the internal organs and tissues. Contrary to this, if the person does not have to bare part of his body for measurement, the adjustment of the thickness of the coverage on the body surface can keep the body surface temperature unchanged with the variation of the ambient temperature, as shown by the group of curves on the right side of FIG. 1A. Furthermore, when a person bares his body for measurement, he will be forced to rely entirely on self adjustment to be adaptive to the changes in ambient temperature and other factors. This physiological inadaptivity will also disrupt the temperature characteristics in the body skin that reflects the level of energy metabolism of the internal organs and tissues. Since nakedness, especially the nudity of the trunk or the chest, is an unnatural human behaviour that runs counter to moral principles, the person in question will feel nervous and out of the place, such psychological inquiety will also disrupt the temperature characteristics in the body skin. Besides, from the physiological point of view, heat generation or metabolism of the various internal organs and tissues will be normal when a person feels warm and comfortable. FIG. 1B shows the results of tests on the sensitivity of a completely nude person to ambient temperature. Only when ambient temperature rises to 31°–34° C. will the human body feel warm and comfortable. However, in such a case, heat dissipates from the human body through evaporation (perspiration), which disrupts the body skin temperature even more severely. In order to avoid heat dissipation by evaporation, maintain relatively high body skin temperature and make a person's body feel warm and comfortable, the following conditions, must be met:

(1) Ambient temperature is below 25° C.;

(2) The part of body for measurement must have a covering of a certain thickness or be covered with suitable clothes so that the temperature difference between the body surface and the covering surface is about 10° C.

When the part of body for measurement, especially the chest or the trunk is covered with clothes (coverings) of suitable thickness instead of being nude, the effects of the variation of ambient temperature, humidity and air flow will be reduced greatly and the physiological and psychological disruption caused by a behaviour violating human moral principles will also be eliminated.

In such conditions (relatively no-interference state), the heat contribution or the micro heat increment in the body skin that reflects the level of energy metabolism of internal organs and tissues are free from the various interferences.

In order to measure the micro heat increment superimposed on the body skin, people tried in a vain attempt to detect the minute temperature difference between various parts of body skin by applying an IR thermometer or thermal imager with an even higher temperature resolution to the coverings on the human body. Such a failure results from the fact that when a thermal imager is used to measure the temperature characteristics in the coverings on the body, the inhomogeneity of the gaps between the body skin and the coverings causes the thermal resistance of the coverings to be inconstant. If the tested person wears tight-fitting clothes to bring his body skin into uniform contact with the coverings, thus enabling the thermal resistance of the coverings to remain constant, the person will feel uncomfortable and have a psychology that affects the collection of the temperature signals. Therefore, presently available thermal imagers and measuring methods cannot be used to measure the micro heat increment superimposed on the body skin and reflecting the energy metabolism of internal organs and tissues.

One of the objects of this invention is to provide a device and method to measure the variation of the IR radiation flux density generated in the human body skin owing to various micro temperature differences (0.01°–0.05° C.) corresponding to an individual internal organ.

Another object of the invention is to provide a device and method to measure from the outside of the coverings on the human body the micro heat increment or micro temperature difference on the surface of the corresponding body skin during the process of energy metabolism of a person's internal organs and tissues when his body feels warm and comfortable without dissipating heat through evaporation.

SUMMARY OF THE INVENTION

In order to realize the above-mentioned purpose, a device of this invention comprises an IR sensor; a display unit connected to the output terminal of said IR sensor; and a test mount, for forming a test area on the human body covering, said mount being so arranged that when in testing, one end of said mount is in contact with the body covering of human body to make the body covering in uniform surface contact with the body skin. A method to realize the above-mentioned interference-free measurement comprises the following steps:
(A) Forming a test area by placing a test mount tightly against the body covering on the tested person's body to make the body covering is in uniform surface contact with the corresponding body skin;
(B) Using an IR sensor for measuring the IR radiation flux density of test area of the tested person's body covering.
(C) Displaying the measurement results.

BRIEF DESCRIPTION OF THE DRAWINGS

FIG. 2 is a diagram showing the configuration of the device of present invention for measuring human body infrared radiation;

FIG. 3 is a section view of the IR sensor incorporated in the human body IR radiation measuring device of present invention;

FIG. 4 is a schematic of the test mount of the measuring device of present invention.

Figure 1A:
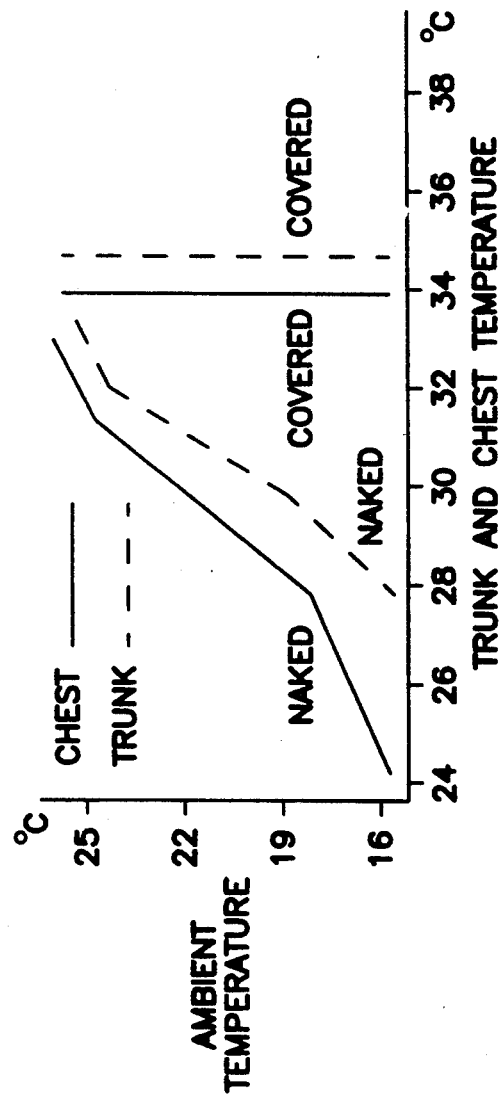
FIG. 1A shows the temperature rise curves of various parts of the body skin at varying ambient temperature for a naked and a covered person.
Figure 1B:
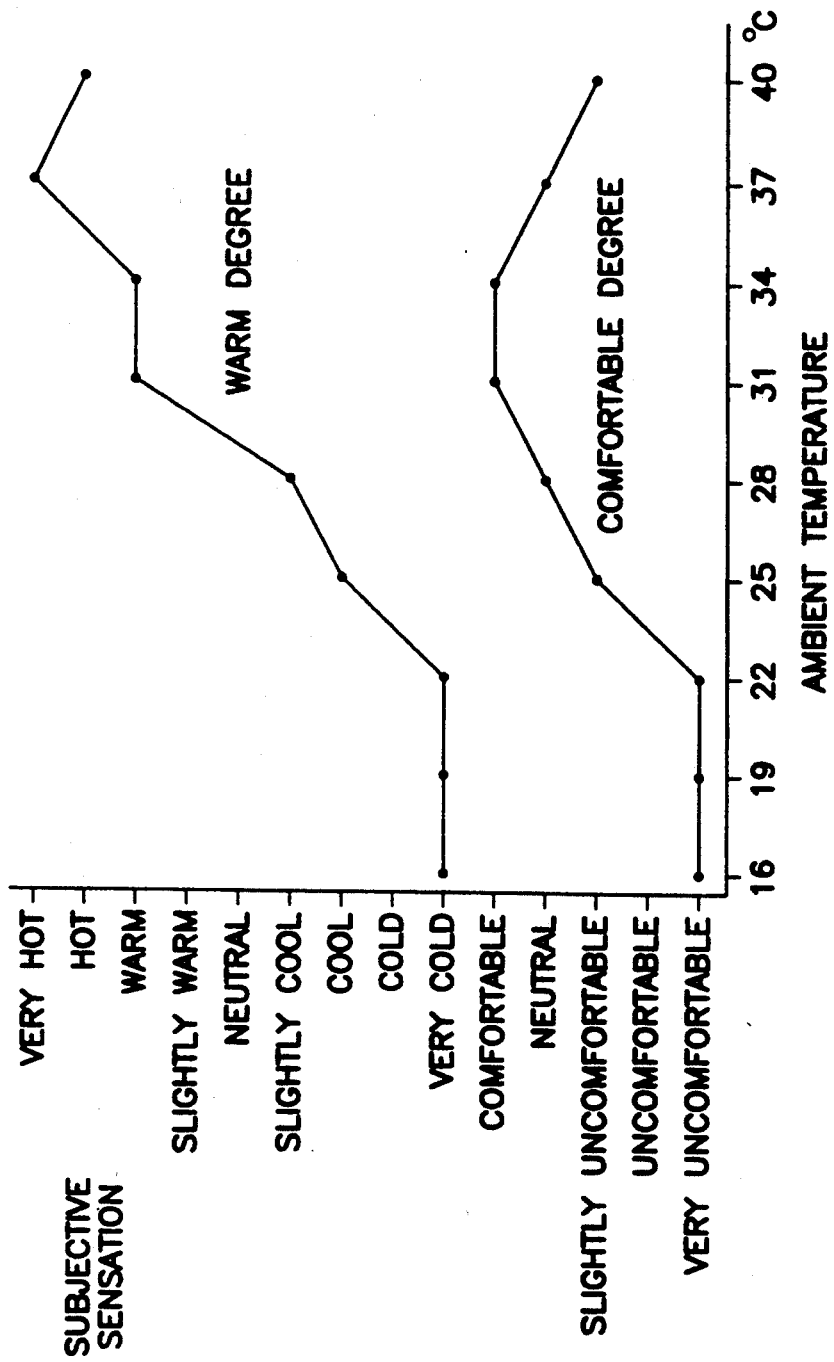
FIG. 1B shows a curve reflecting the adaptability of the person's skin to ambient temperature when the person is completely naked.

In these figures identical components and components of the same type are designated by same reference.

DETAILED DESCRIPTION OF THE INVENTION

According to present invention, the device of the invention comprises an IR sensor; a display unit connected to the output terminal of said IR sensor; and a test mount, for forming a test area on the human body covering, said mount being so arranged that when in testing, one end of said mount is in contact with the body covering of human body to make the body covering in uniform surface contact with the body skin. FIG. 2 shows a test mount 4 whose legs 1 are tightly pressed against covering 3 on body skin 2, IR sensor 6 being connected to display 8 through cable 7. During a test, legs 1 of mount 4 are tightly pressed against body covering 3 so that body covering 3 and body skin 2 are in close surface contact with each other and that a tightly pressed area (i.e. test area) 9 is formed between these legs 1. Within the tightly pressed area 9, uniform surface contact occurs between body covering 3 and body skin 2 to enable the heat resistance of the body covering to remain constant. The tightly pressed area should not be smaller than the area of the field of view projected on the test area through detecting opening 10 by the sensing element 11 (FIG. 3) incorporated in IR sensor 6. The tightly pressed area 9 should be located in the specific positions corresponding to the various internal organs. Temperature characteristics of internal organs or tissues in the said tightly pressed skin area 9 can be transmitted through IR sensor 6 and transmission cable 7 to display 8. The tightly pressed area 9 acquires heat from outside radiation sources while losing heat through radiation and therefore, the IR radiation flux received by IR sensor 6 will be IR radiations emitted from and absorbed by tightly pressed area (test area) 9. The heat radiation absorbed by tightly pressed area (test area) 9 is taken as the background temperature (acquiring radiation) in IR sensor 6, which measures the temperature difference produced by the IR radiation energy emitted from the various tightly pressed areas 9 relative to the said background temperature (acquiring radiation). In order to maintain the background temperature, the detecting opening 10 of IR sensor 6 is normally located on the same axis as the tightly pressed area 9 and the distance between IR sensor 6 and tightly pressed area 9 should be at least greater than 3 cm. In the embodiment of the present invention, the outer wall 13 of detecting opening 10 of IR sensor 6 is connected to the thread at one end 5 of mount 4 (FIG. 4). In order to keep the IR radiation emitted from and absorbed by the tightly pressed area 9 free from interference, the number of legs 1 of mount 4 are in many cases reduced. In the embodiment of the present invention, the test mount has two pressing legs.

As shown in FIG. 3, IR sensor 6 includes an IR sensing element 11 which is able to resolve the variation of IR radiation flux density inconnection with temperature differences of a magnitude of 0.01° C. Sensing element 11 is enclosed in a copper sleeve 12 which is made of interference-resistant and high heat-conductive material, and the case of the sensing element 11 is in contact with the copper sleeve 12. Low heat-conductive materials such as polystyrene 16 is filled between the copper sleeve 12 and plastic case 15 to enhance the resistance against the interference of the thermal environment. The said IR sensor 6 has a detecting opening 10, the outer wall of which incorporates an outer thread 13. When IR sensor 6 is not working, the internally threaded cap 14 can be placed over the detecting opening 10 of IR sensor 6. During the operation of IR sensor 6, the cap should be removed and mount 4 should be fixed in its place as shown in FIG. 4. End 5 of mount 4 should be tightly screwed onto the external thread 13. The area between each leg 1 at the other end of mount 4 should be at least larger than the area of the field of view projected on covering by the detecting opening 10 of IR sensor 6. The sensing element 11 inside the IR sensor 6 is connected to display 8 via cable 7 (FIG. 2).

The test mount 4 as shown in FIG. 4 is made of thin metal strap covered on the outside with plastic material. End 5 of the said mount is bent into the shape of a spiral with an internal diameter equal to the neck diameter of IR sensor 6. The legs of mount 4 are normally made to stand out in shape of a horn. The distance between legs 1 is slightly greater than the diameter of the field of view projected on test area 9 through detecting opening 10 by the IR sensor 11, the optimum leg span being greater than the diameter of the said field of view by 0.5 to 1 cm. In order to maintain the dynamic balance between the background temperature (acquiring radiation) and the environment, the said mount should be of a length of at least 3 cm.

In order to measure the temperature characteristics of a human body correctly, the tested person must be statically placed in such natural conditions that his body skin feels warm and comfortable; in other words, the person being tested must have a covering on his body to prevent body heat from dissipating quickly. More specifically, the person should wear suitable clothes, and in such conditions that heat exchange takes place between the human body and the outside world through the body covering and skin temperatures of various parts of the body are kept at such levels that the body is in the natural warm and comfortable state.

The mathematical model for finding out the skin temperature Ts of a human body by measuring the temperature of the outer surface of the covering on the human body is as follows;

$$CcL = Cr + Ccv + Ccd \quad (1)$$

where $$CcL(W/cm^2) = \frac{Ts - TcL}{0.16\,RcL} \quad (2)$$

$$Cr(W/cm^2) = \epsilon cL\, \sigma\, TcL^4 \quad (3)$$

Ccl is the heat loss on the surface of the covering on the human body;
Cr is the heat loss by radiation on body surface;
Ccv is the heat loss due to convection;
Ccd is the heat loss due to conduction;
Ts is the temperature on the surface of the skin;
Tcl is the temperature on the outer surface of the covering on the human body;
Rcl is heat resistance between the surface of the body skin and the surface of the covering;
$\epsilon cl$ is the surface radiation coefficient of the covering on the human body;
$\sigma$ is the Stefan-Boltzman constant.

When the ambient temperature and the heat resistance of the covering on the human body are both fixed and there is not strong air flow, equation (1) can be simplified as $$Ccl = Cr + Cg \quad (4)$$

where Cg is a constant and equals to the sum of Ccv and Ccd as evidenced by substituting equations (2), (3) and (4) into equation (1).

We also have $$Ts = 0.16 Rcl(\epsilon cl \sigma T^4 cl + Cg) + Tcl \quad (5).$$

From equation (5) we find that when heat resistance Rcl is fixed and $\epsilon cl$, $\sigma$ and Cg are all constant, the skin temperature of a human body Ts is only a one-dimensional function of the independent variable Tcl. Thus, after we have measured the variation of the flux density of the IR radiation for different temperatures of Tcl on the outer surface of the covering (such as a coat) on the human body, we should be able to calculate the actual temperature on the body surface.

According to the invention, the method of present invention comprises the steps as follow:

(A) Forming a test area by placing a test mount tightly against the body covering on the tested person's body to make the body covering is in uniform surface contact with the corresponding body skin;
(B) Using an IR sensor for measuring the IR radiation flux density of test area of the tested person's body covering.
(C) Displaying the measurement results.

As shown in FIG. 2, the tightly pressed area 9 formed by pressing legs 1 of mount 4 against the body covering made the heat resistance Rcl a constant and is not large enough to alert the tested person that he is being tested; therefore there will be no interference of physiological and psychological factors caused inconvenience. Since the length of the legs of the mount is at least 3 cm, the acquired heat radiation (background temperature) of the test area 9 will not be affected, and therefore the accuracy of the measurement is guaranteed. IR radiation in each tightly pressed area (test area) 9 is measured at equal distances from the tightly pressed area 9 to IR sensor 6. The measured signals are transmitted to display 8 via cable 7 and read out in digital form. An optimum condition is that the distance on the axis passing through IR sensor 6 and the tightly-pressed area 9 is 10 cm.

I claim:

1. A device for measuring an IR radiation flux density of a human body, comprising:
   an IR sensor having a plastic case, and an IR sensing element disposed in the plastic case, the plastic case having a detecting opening;
   a display unit electrically connected to an output terminal of said IR sensor through a cable wherein one end of the cable connects to the display unit, and an other end of the cable connects to the output terminal;
   a test mount, with a first end of said mount being connected to the plastic case of said sensor, and a second end of said mount having leg means for making contact with a human body covering, the leg means including at least two legs;
   wherein each of the legs of said test mount is tightly pressed against the covering on a tested person's body, bringing the human body covering between said legs into close contact with skin of the human body and forming a tightly pressed test area between said pressing legs, and in said tightly pressed test area said human body covering being in uniform contact with said human body skin to enable thermal resistance of said human body covering to remain constant;
   wherein said tightly pressed test area should be at least larger than an area of a field of view projected on said test area through the detecting opening by said sensing element of said sensor and, in order to maintain a background temperature of said test area and enable said test area to acquire radiated heat while losing heat through radiation, said detecting opening of said IR sensor is normally located on the same axis as said tightly pressed test area, and an axial distance between said IR sensor and said tightly pressed test area should be at least greater than three cm;

an external thread on an outer wall at a neck of the detecting opening of the plastic case being connected to a thread in the first end of said mount; and said mount being made of a thin metal strip covered on an outside with plastic material, with the first end of said mount being coiled into a spiral form with its inner diameter matching with the external thread on the outer wall of said detecting opening, and extremities of the legs at the second end of said mount being bent either inward or outward.

* * * * *